United States Patent
Berthold (12)

(10) Patent No.: US 6,519,041 B1
(45) Date of Patent: Feb. 11, 2003

(54) HYDROGEN SENSOR FOR FUEL CELL APPLICATIONS

(75) Inventor: John W. Berthold, Salem, OH (US)

(73) Assignee: j w b c. llc, Salem, OH (US)

(*) Notice: Subject to any disclaimer, the term of this patent is extended or adjusted under 35 U.S.C. 154(b) by 210 days.

(21) Appl. No.: 09/606,450

(22) Filed: Jun. 29, 2000

(51) Int. Cl.[7] .................................................. G02B 9/02
(52) U.S. Cl. ........................ 356/477; 356/478; 385/12
(58) Field of Search ................................. 356/445, 477, 356/478, 480; 250/227.19, 227.27; 385/12

(56) References Cited

U.S. PATENT DOCUMENTS 5,153,931 A * 10/1992 Buchanan et al. ............ 385/12

OTHER PUBLICATIONS

M.A. Butler "Optical Fiber Hydrogen Sensor" Nov. 15, 1984, Applied Physics Letters 45 (10) pp. 1007–1009.*
M.A. Butler, "Optical Fiber Hydrogen Sensor," Appl. Phys. Lett. 45 (10), Nov. 15, 1984, pp. 1007–1009, © American Institute of Physics, 1984.

* cited by examiner

Primary Examiner—Samuel A. Turner
Assistant Examiner—Patrick Connolly
(74) Attorney, Agent, or Firm—Robert C. Baraona

(57) ABSTRACT

An intrinsically safe fiber optic hydrogen sensing assembly for detecting hydrogen levels in a system and/or for detecting hazardous hydrogen concentration gas leaks therefrom is disclosed. The sensor assembly preferably uses a palladium coated end of the fiber optic cable as the hydrogen sensor based upon the intensity and phase of the light reflecting off of the coated end. The assembly may be constructed to control the flow of hydrogen to the system and/or to sound an alarm indicative of leakage of hydrogen from the system.

12 Claims, 2 Drawing Sheets

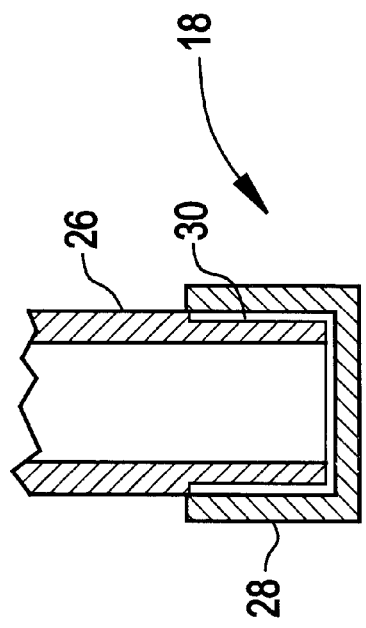
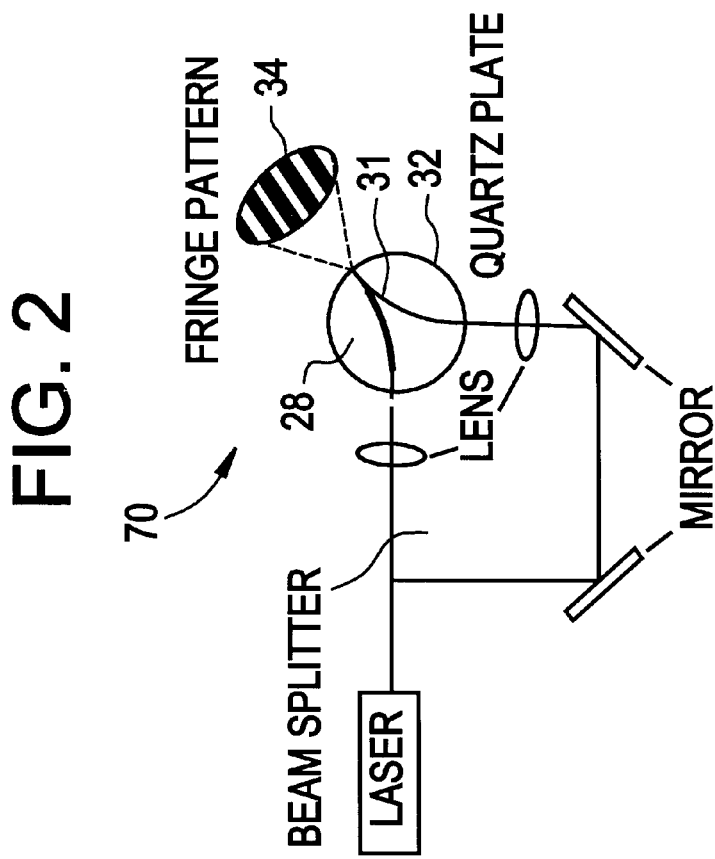

HYDROGEN SENSOR FOR FUEL CELL APPLICATIONS

BACKGROUND OF THE INVENTION

1. Field of the Invention

The present invention generally relates to hydrogen sensors and more particularly to such sensors being used to detect hazardous hydrogen buildup conditions in and around a fuel cell.

2. Description of the Prior Art

As fuel cell applications become more widespread, the need for hazardous hydrogen concentration sensing in and around such fuel cells becomes necessary. Specifically, a 4% hydrogen concentration in air constitutes an explosive mixture. Accordingly, a hydrogen sensor is needed to monitor fuel cell assemblies for hydrogen fuel leaks.

Numerous methods to detect hydrogen exist. The methods range from expensive, high sensitivity instruments (gas chromatographs and mass spectrometers capable of detection of sub-parts per million) to low-cost, simple methods such as a pair of thermocouples operated in differential mode with one of the thermocouples coated with a catalyst. None of these methods are suitable for use in or around a solid oxide fuel cell stack. Laboratory instruments such as mass spectrometers are not capable of in-situ operation and cannot operate in a continuous, unattended manner. Thermocouples can operate in-situ, but tend to drift at solid oxide fuel cell operating temperatures of 900° C. Furthermore, the catalyst coatings used in the hydrogen detectors can be poisoned by even small amounts of CO or $SO_2$ gases which may be present in some fuel cell fuels. Plus, since thermocouples are electrical devices, they are not intrinsically safe, insofar as they constitute an arc and spark hazard and an impractical ground fault protector would be needed to use them in environments where an explosion hazard exists.

What is ultimately needed for hydrogen detection is a low-cost, low-drift in-situ sensor that can function for thousands of hours of continuous use in a high temperature environment, and which is capable of repeatable measurement of hydrogen concentration in the 1 to 10% range. It is also very desirable that the hydrogen sensor be intrinsically safe.

SUMMARY OF THE INVENTION

The basic configuration of the invention consists of an optical fiber connected at one end to a signal conditioning and processing unit. Light from the signal conditioner is transmitted through the fiber to the opposite (terminal) end of the fiber, which defines the hydrogen sensor location. The terminal end is coated with palladium (Pd) metal which acts as a reflector to return light to the input end. The optical constants (refractive index and absorption coefficient) of Pd change when it is exposed to hydrogen. The Pd metal also swells as it soaks up hydrogen much, like a sponge soaks up water.

The changes in the optical constants of Pd, which consequently affect the intensity and phase of light reflected back into the fiber optic cable, are utilized in some embodiments of the present invention. Specifically, the change in refractive index of the glass fiber, which occurs as a result of the stress induced by the swelling Pd, is employed. When the optical constants of Pd change, the optical phase shift of the reflection changes; similarly, when the stress in the fiber changes (due to Pd swelling), the fiber's refractive index changes in proportion to the stress which, in turn, alters the phase of an optical signal traveling through the stressed portion of the fiber. Ultimately, these aforementioned changes can be detected by measurement of the resultant phase shift of light reflected back to the signal processor.

A two-beam interferometer can be used to detect the phase shift with the interference occurring at the photodetector in the signal processor unit. The interferometer compares the light entering the fiber with the light reflected by the Pd coating. Using electronic methods and components well known to those skilled in the art, the magnitude of the phase shift is converted to a signal voltage that changes in proportion to changes in the phase shift. The sensitivity and dynamic range are more than adequate to detect changes in hydrogen concentration of 4%, and provide sufficient margin to set an alarm threshold.

In view of the foregoing it will be seen that one aspect of the present invention is to detect a hazardous hydrogen concentration in any system which employs hydrogen gas, and especially in and around a fuel cell.

Another aspect is to provide an intrinsically safe hydrogen sensor, with particular utility for detecting fuel cell leaks.

Yet another aspect is to provide a multiplexed hydrogen leak sensor system, again with particular utility for detecting hydrogen in a plurality of fuel cells.

Accordingly, a fiber optic hydrogen sensor, for sensing the overall hydrogen concentration in a system which utilizes a gas mixture at least partially composed of hydrogen gas is disclosed. The sensor comprises a fiber optic cable, with a reflective, coated end and with a specific type of light passing through it, and means for detecting changes in the intensity and/or phase of the reflected light which is representative of the overall hydrogen concentration in the part of the system which is being monitored. Additionally, the sensor may use a palladium coating for the fiber optic cable, a photodector, an interferometer, a light coupler, a 2×2 light splitter, an alarm and/or automated control valves. Ideally, the sensor may be used on one or more fuel cells (or other, repeating units in a system). Finally, where appropriate, the sensor may also utilize a set point in order to compare the measured signal against a known standard of hydrogen concentration.

These and other aspects of the present invention will be more fully understood upon a review of the following description of the preferred embodiment when considered in conjunction with the drawings.

DESCRIPTION OF THE DRAWINGS

In the drawings:

FIG. 2 is a schematic of a Mach-Zehnder interferometer used in one embodiment of the present invention; and FIG. 3 is an expanded view of the sensing end of the sensor depicted in FIG. 1.

DESCRIPTION OF THE PREFERRED EMBODIMENTS

Figure 1:
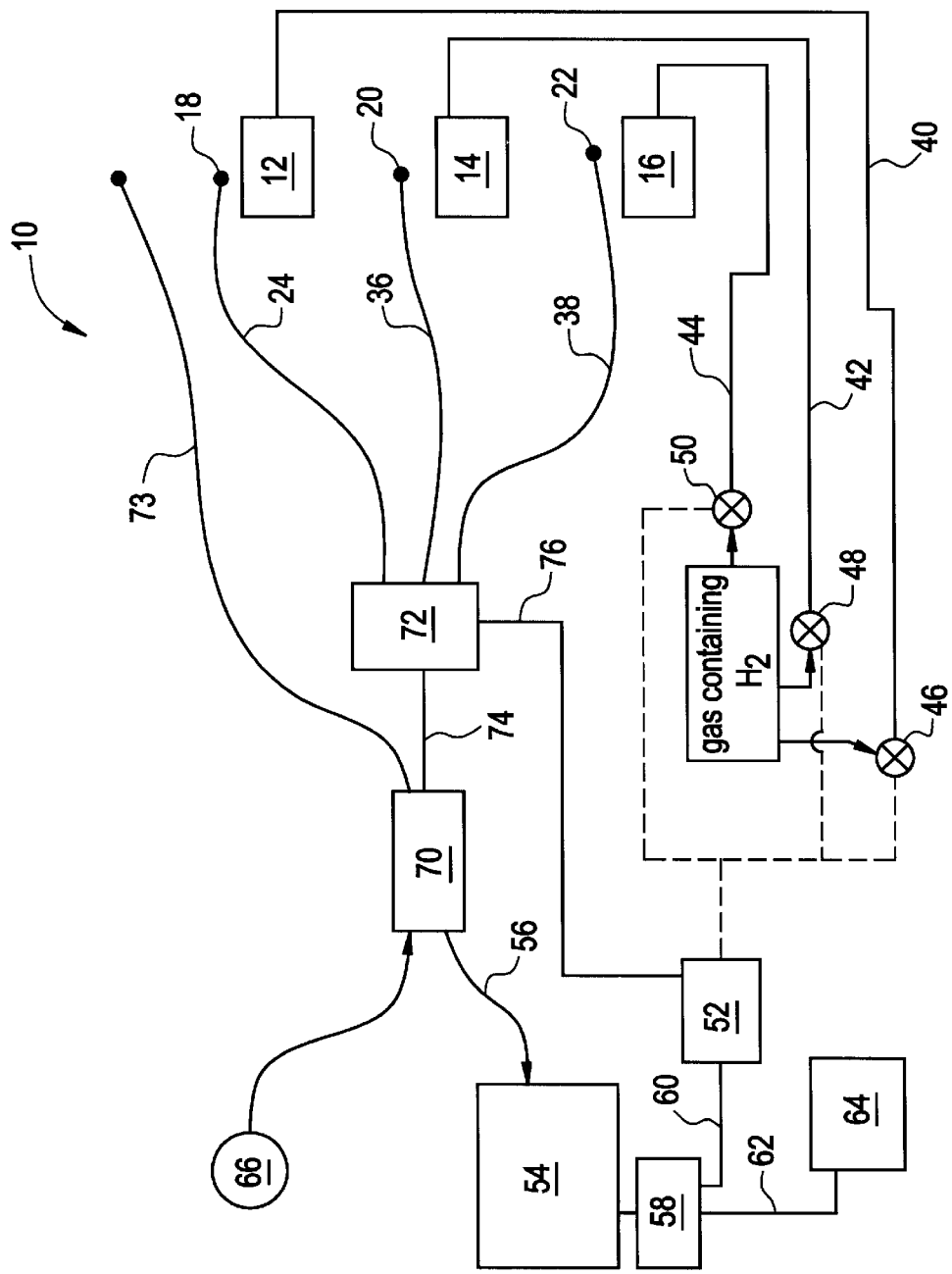
FIG. 1 is a schematic of fiber optic hydrogen sensor system of the present invention.

Referring now to the drawings and particularly to FIG. 1, a fiber optic hydrogen sensing assembly (10) is shown for detecting the overall hydrogen gas concentration in a system, here shown as a plurality of similar units (12, 14, 16), which preferably could be fuel cells. Each unit has a strategically located hydrogen sensor (18, 20, 22). While the hydrogen sensors are shown externally located around the unit to detect hydrogen concentration therein, it will be understood that they could just as easily be sealably located inside each unit to detect the hydrogen concentration inside the unit. An advantage to this internal setup is that the sensor itself does not pose any explosive danger in the event that it comes into contact with hydrogen.

The construction of the sensor (18, 20, 22) is best seen in FIG. 3, where only one sensor (18) is shown (but which is representative of any of the sensors described herein). Sensor (18) comprises a simple coated optical fiber cable (26), a coating (28), and an optional adhesive layer (30). The actual sensing element is located on coated end (28). Sensor (18) utilizes the physical properties of the coated end (28), which preferably contains palladium and must, in any event, change in a uniform, consistent fashion when exposed to hydrogen. In particular, if Pd is used, the optical constants of any light reflected off of coated end (28) will change in a consistent, predictable manner (discussed below).

Again with reference to FIG. 3, the sensing element itself is a piece of standard, communications-grade, single mode optical fiber (26). The plastic jacket is stripped off of one end of fiber (26) and a thin (10 um) palladium coating (28), about 3 cm long, is applied thereto. The coating (28) may be applied by first depositing an adhesive layer in between the fiber (26) and the coating (28), such as by sputtering in argon with an initial 10 nm-thick titanium layer (30), although any known, compatible adhesive should suffice. If the phase shift on reflection is used to practice the present invention, then adhesive layer (30) must be transparent.

Exposure of a palladium-based coating (28) to hydrogen gas results in the formation of the hydride $PdH_x$, with x being dependent on the partial pressure of hydrogen. The hydride has a lattice constant which depends on x, and which is necessarily larger than pure palladium. However, this dependency is a reversible process and may be represented by the thermodynamic equilibrium in Equation (1) below:

$$\log(P^{1/2}) = \log(x) + 4.2 - \frac{521.9}{T} - \frac{926x}{T-215} \qquad \text{Equation (1)}$$

where:
P=partial pressure of hydrogen
T=absolute temperature
x=hydride composition Equation (1) describes the relationship between the hydrogen partial pressure P and the hydride composition x. Below 1 Torr of hydrogen gas, which corresponds to x~0.004, the relationship becomes $P^{1/2}=Ax$, where A is a constant only dependent on T. This square root dependence of hydride composition on pressure results in a substantial sensitivity over a wide dynamic range. The expansion of the hydride stretches the fiber in both axial and radial directions, and it further changes the refractive index and, thus, the effective optical path length of light traveling through the fiber. This effect may be demonstrated by inclusion of the sensor (28) in one arm of a Mach-Zehnder interferometer, as shown in FIG. 2.

In FIG. 2, interferometer (70) has both ends of the coated (28) and uncoated fiber (31) glued to a fused quartz plate (32), using Eastman 910 adhesive or other suitable means. The plate (32) is then enclosed in a glass chamber (not shown) through which the hydrogen-containing gas mixture flows. Movement of the fringe pattern (34) can be observed using a simple photodetector and chart recorder (not shown) in order to monitor variations in the hydrogen concentration. In the event that an undesirable concentration or leak is detected, a suitable alarm could be triggered, an automatic or manual shutoff could be initiated, or a simple output device can't record the event. Significantly, use of this interferometer can substantially simplify the hydrogen sensing system contemplated in this invention.

In the embodiment shown in FIG. 1, light coupler (70) may be a 2×2 optical power splitter that divides light from the modulated source (66) equally between two output fibers—reference fiber (73) and test fiber (74). Notably, the interferometer of FIG. 1 is preferably a two-beam interferometer or a Michelson interferometer. Light travels down both pathways and is then reflected back for processing, as described below. Those skilled in the art will readily appreciate the possible variations in configuration of the system, depending upon how many sensors are used.

Reference fiber (73) is an interferometric reference fiber which provides a constant optical path. The terminal end of fiber (73) is coated with any appropriate reflective material that returns light to photodetector (54). The length of reference fiber (73) is chosen to be approximately equal to the lengths of fibers (24, 36, 38) so that the difference in length between reference fiber (73) and any of the other sensor(s) is less than the coherence length of the light source (66).

In the embodiment of FIG. 1, light source (66) provides an unmodulated or modulated input light signal to the system. Preferably, light source (66) is a near-monochromatic laser. If the coherence length condition is fulfilled, then light reflected from any one of the palladium coatings at sensors (18, 20, 22) interferes with the reflected light from the terminal end of reference fiber (73), thereby producing an electrical output current which changes in proportion to the light power (this occurs when the interference is detected by photodector (54)). Changes in light power result from changes in optical phase which, in turn, result from changes in the palladium coating caused by the presence of hydrogen.

In the embodiment of FIG. 1, it is assumed that the optical path through reference fiber (73) is constant and that changes in temperature of the sensor fiber do not introduce phase errors into the sensor light signals. In general, phase errors caused by temperature changes can be large; accordingly, those skilled in the art will appreciate that additional methodology must be employed to reduce temperature errors when practicing this embodiment of the present invention. Such methodologies may include (but are not limited to): the use of polarization preserving optical fiber, the use of an additional light source to inject a second light signal at a different wavelength to provide an error correction signal for temperature changes, and/or any other method known to those skilled in the art.

Each unit (12, 14, 16) is supplied with a hydrogen-containing gas via lines (40, 42, 44). The supply of the hydrogen containing gas is provided through respective control valves (46, 48, 50), which optimally are independently controlled by a controller (52). The controller (52) is responsive to photodetector (54) through conditioning interface circuits located in signal conditioner and processor (58). As the multiplexer (72) is cycled, the photodetector (54) separately receives reflected light signals from reference fiber (73) and from one of the sensors (18, 20, 22) as a combined input signal along fiber optic line (56). After photodetection (conversion of light signal to electrical signal), the electrical input signal from each sensor (18, 20, 22) is compared to a set point signal of specific hydrogen concentration, preferably stored in the electronic memory of signal conditioner/processor (58). For multiple concentration measurement, more than one set point could be used. In any case, the comparison of set point signal to input signal establishes an output signal, transmitted along output electrical lines (60, 62) which is indicative of the hydrogen concentration measured by the individual sensors (18, 20, 22).

When any unit (12, 14, 16) indicates an undesirable hydrogen concentration, the output signal could activate an alarm assembly (64) and the flow of fuel to the leaking fuel cell may be shut off manually by closing the appropriate valve (46, 48, 50). As above, controller (52) could automate this shut off procedure. Further, a simple output device (not shown), such as a chart recorder, computer, or display, unit may also be employed in the system. Notably, use of alarm (64), controller (52), and/or output device(s) may be simultaneously, partially or selectively used (i.e., only one, any combination of two, or all three may be used at any given moment).

As mentioned above, one output from light coupler (70) is connected to a multiplexer (72) by fiber optic cable (74). The multiplexer (72) transmits the light from the source (66) to all three sensors (18, 20, 22) in sequence and passes the respective reflected light therefrom back to the photodetector (54) via fiber optic line (56). This light signal is coupled with an identifying signal of the corresponding multiplexed sensor along electrical line (76) to controller (52), thereby allowing controller (52), or other device, to perform a function, such as shutting off the appropriate valve (46, 48, 50).

The multiplexer (72) may use either time division multiplexing with a single pulsed light source, or wavelength division multiplexing of multiple light sources, or a combination of both methods can be used as the multiplexing scheme to obtain near-simultaneous measurements from the several Pd coated optical fiber sensors (18, 20, 22) connected to the detector (54).

As previously noted, the palladium coating changes the transmissivity of the fiber optic cable, consequently permitting a comparison of the change by a signal conditioner and processor against an appropriate set point. In turn, if the compared values approach a set point, the system activates the appropriate valve and/or alarm.

The effect of hydrogen is reversible and a similar behavior is observed when hydrogen is removed from the Pd film coated sensor. This phenomena permits real-time monitoring of both increases and decreases in the hydrogen concentration.

It will be understood that while only the sensing operation for sensor (18) and fiber optic cable (24) has been described, the foregoing is equally applicable to sensors (20, 22) and fiber optic cable (36, 38). As mentioned before, the system may be used to monitor any number of units, and the addition or elimination of such units would result in a corresponding alteration of the system elements. For example, if only one unit is provided for hydrogen sensing, the need for multiplexing is eliminated.

In view of the foregoing it will be seen that the present hydrogen concentration sensor system provides:

1. Hydrogen sensors consisting of fused silica (glass) and/or sapphire (aluminum oxide) optical fibers and palladium metal coating(s) which enable continuous sensor operation at 800° C. temperatures—the typical temperature for solid oxide fuel cells, thereby permitting measurement of hydrogen levels in or around a fuel cell(s).
2. Reflected light signals from several optical fibers, each associated with a particular unit and each having palladium sensor coating(s) (or other appropriate coatings which do not depart from the principles discussed herein), may be multiplexed into one signal conditioner processor for monitoring and/or control of the observed units.
3. A hydrogen sensor using optical fibers which are not electrically conductive, and hence are intrinsically safe compared to electrically conductive thermocouple wires.

Certain modifications and additions will occur to those skilled in the art upon reading this disclosure. It will be understood that all such were deleted herein for the sake of conciseness and readability but are intended to fall within the scope of the following claims.

I claim:

1. A fiber optic hydrogen sensor, for sensing the overall hydrogen concentration in a system which utilizes a gas mixture at least partially composed of hydrogen gas, comprising:

a fiber optic cable positioned proximate to a selected area of a system, wherein the system comprises at least one fuel cell, and having a light, with a measurable intensity and a measurable phase passing therethrough, and a coated end for reflecting the light; and means for detecting a change, which is representative of the overall hydrogen concentration in the selected area of the fuel cell system, in at least one of: the intensity of the reflected light and the phase of the reflected light.

2. A fiber optic hydrogen sensor as set forth in claim 1, wherein the fuel cell is sealed and the coated end of the fiber optic cable is strategically located on the fuel cell to detect any hazardous leakage of hydrogen gas in the selected area of the fuel cell.

3. A fiber optic hydrogen sensor, for sensing the overall hydrogen concentration in a system which utilizes a gas mixture at least partially composed of hydrogen gas, comprising:

a fiber optic cable positioned proximate to a selected area of the system and having a light, with a measurable intensity and a measurable phase passing therethrough, and a coated end for reflecting the light;

a photodetector having an output signal indicative of at least one of: the intensity of the reflected light and the phase of the reflected light;

means for processing and comparing the output signal to a set point, wherein the set point is representative of a specific hydrogen concentration; and means for selectively controlling the gas mixture provided to the system which is responsive to at least one of: the output signal and the overall hydrogen concentration in the selected area of the system.

4. A fiber optic hydrogen sensor as set forth in claim 3, wherein the means for selectively controlling the gas mixture provided to the system comprises at least one controllable valve which decreases the hydrogen gas provided to the system and wherein control of the valve is directly related to at least one of: the output signal and the overall hydrogen concentration in the selected area of the system.

5. A fiber optic hydrogen sensor, for sensing the overall hydrogen concentration in a system which utilizes a gas mixture at least partially composed of hydrogen gas, comprising:

a fiber optic cable positioned proximate to a selected area of the system and having a light, with a measurable intensity and a measurable phase passing therethrough, and a coated end for reflecting the light;

means for detecting a change, which is representative of the overall hydrogen concentration in the selected area of the system, in at least one of: the intensity of the reflected light and the phase of the reflected light; and means for selectively controlling the gas mixture provided to the system which is responsive to the overall hydrogen concentration in the selected area of the system.

6. A fiber optic hydrogen sensor as set forth in claim 5, wherein the means for selectively controlling the gas mixture provided to the system comprises at least one controllable valve which decreases the hydrogen gas provided to the system and wherein control of the valve is directly related to the overall hydrogen concentration in the selected area of the system.

7. A fiber optic hydrogen sensor as set forth in claim 1, wherein the means for detecting a change further comprises an alarm assembly and wherein the alarm assembly is responsive to and indicative of a specific concentration of hydrogen gas in the selected area of the system.

8. A fiber optic hydrogen sensor as set forth in claim 3, further comprising an alarm assembly and wherein the alarm assembly is responsive to and indicative of a specific concentration of hydrogen gas in the selected area of the system.

9. A fiber optic hydrogen sensor as set forth in claim 1, wherein the means for detecting a change comprises an interferometer.

10. A fiber optic hydrogen sensor as set forth in claim 9, wherein the interferometer comprises a two-beam interferometer.

11. A fiber optic hydrogen sensor as set forth in claim 9, wherein the interferometer comprises one of: a Mach-Zender interferometer and a Michelson interferometer.

12. A fiber optic hydrogen sensor as set forth in claim 1, wherein the means for detecting a change further comprises an output device for monitoring the overall hydrogen concentration of the selected area of the system.

* * * * *